US00PP14423P39

(12) United States Plant Patent
Paduch

(10) Patent No.: US PP14,423 P3
(45) Date of Patent: Dec. 30, 2003

(54) RHIPSALIDOPSIS PLANT NAMED 'LAUREN'

(50) Latin Name: *Rhipsalidopsis rosea*
Varietal Denomination: Cactaceae

(75) Inventor: Louis Paduch, Carver, MA (US)

(73) Assignee: Bay City Flower Company, Half Moon Bay, CA (US)

( * ) Notice: Subject to any disclaimer, the term of this patent is extended or adjusted under 35 U.S.C. 154(b) by 0 days.

(21) Appl. No.: 10/026,058

(22) Filed: Dec. 24, 2001

(65) Prior Publication Data

US 2003/0121088 P1 Jun. 26, 2003

(51) Int. Cl.[7] ..... A01H 5/00

(52) U.S. Cl. ..... Plt./372

(58) Field of Search ..... Plt./372

*Primary Examiner*—Bruce R. Campell
*Assistant Examiner*—Annette H. Para
(74) *Attorney, Agent, or Firm*—Charles R. Cypher; James R. Cypher

(57) ABSTRACT

A new and distinct plant variety of the Cactaceae family produced in a controlled hybridization named Rhipsalidopsis 'Lauren'. Rhipsalidopsis 'Lauren' has a strong growth habit, a "pinkish" colored bloom, a strong propensity to branch with minimal pruning, erect stems, and flowers stay open for two weeks.

3 Drawing Sheets

Latin name of the genus and species of the plant claimed: The new variety is a hybrid plant in the Rhipsalidopsis genus. A species determination has not been made.

Variety denomination: The new plant has been given the varietal designation 'Lauren' by the inventor.

BACKGROUND OF THE INVENTION

The present invention relates to a new and distinct variety of the Cactaceae family. The new variety is a Rhipsalidopsis hybrid named 'Lauren' by the inventor. The inventor is Louis Paduch of Carver, Mass., a citizen of the United States.

Many members of the Cactaceae family tend to bloom in the months of November and December in the Northern Hemisphere. Because of their blooming time, there is a large market for these varieties during the Thanksgiving and Christmas seasons as a decorative plant.

This new variety was produced by the inventor by a controlled hybridization process of cross-pollinating selected individual plants.

The overall pink appearance of the flower is due to the generally even-toned color of its petals.

The distinguishing characteristics of the new variety are retained by asexually reproduced, successive generations.

The new variety possesses the commercially desirable characteristics of:

1. a strong growth habit with erect stems;
2. a "pinkish" colored bloom;
3. a strong propensity to branch with minimal pruning; and
4. flowers that stay open for as long as two weeks.

The new variety has asexually reproduced under the direction of the inventor at a commercial nursery in Half Moon Bay, Calif. through three successive generations by cuttings, and it has been found that the combination of characteristics as herein disclosed remain firmly fixed.

BRIEF DESCRIPTION OF THE DRAWING

The accompanying drawings serve, by color photographic means, to illustrate the new plant variety. The colors are represented as truly as possible using conventional photographic procedures.

DETAILED DESCRIPTION OF THE NEW VARIETY

Figure 1:
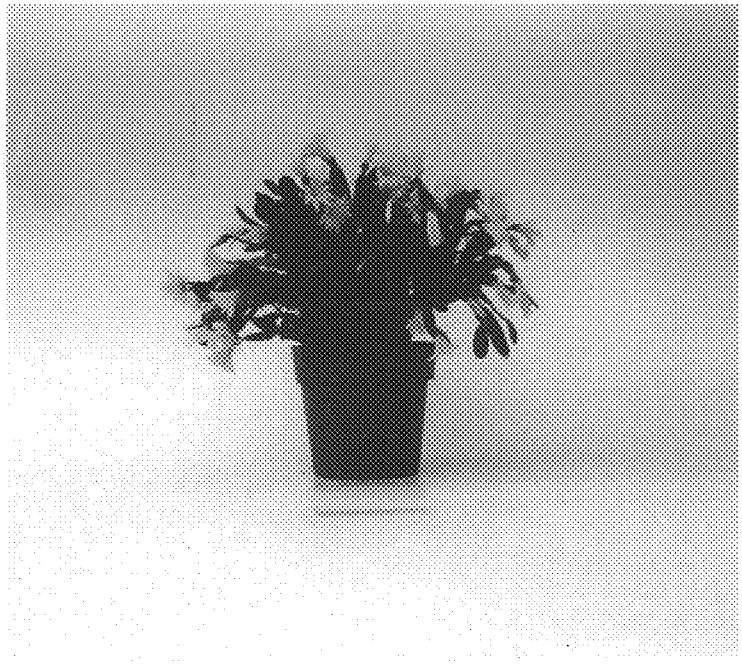
FIG. 1 is a color photograph of several individuals of the new variety illustrating the overall appearance and form of the plants, and the abundance of blooms, when grown in a single pot for commercial sale.
Figure 2:
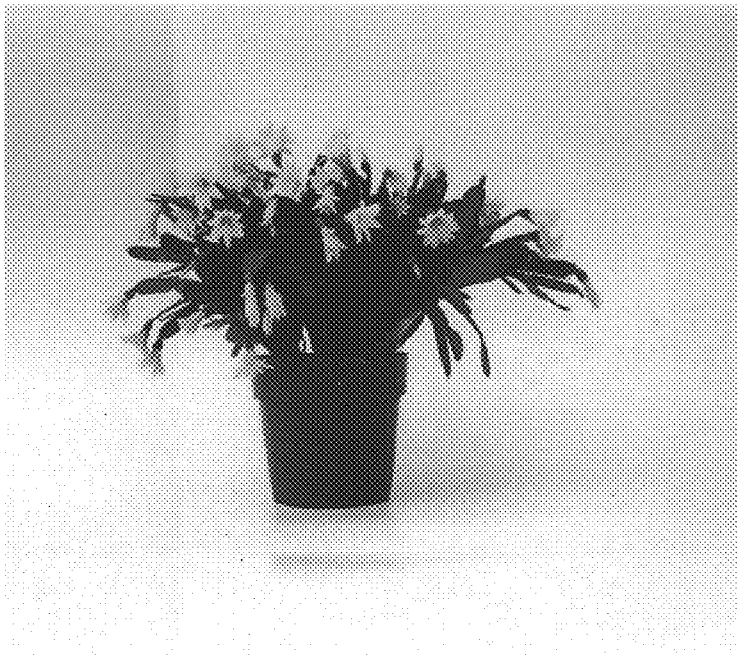
FIG. 2 is a color photograph of several individuals of the new variety illustrating the overall appearance and form of the plants, and the abundance of blooms, when grown in a single pot for commercial sale.
Figure 3:
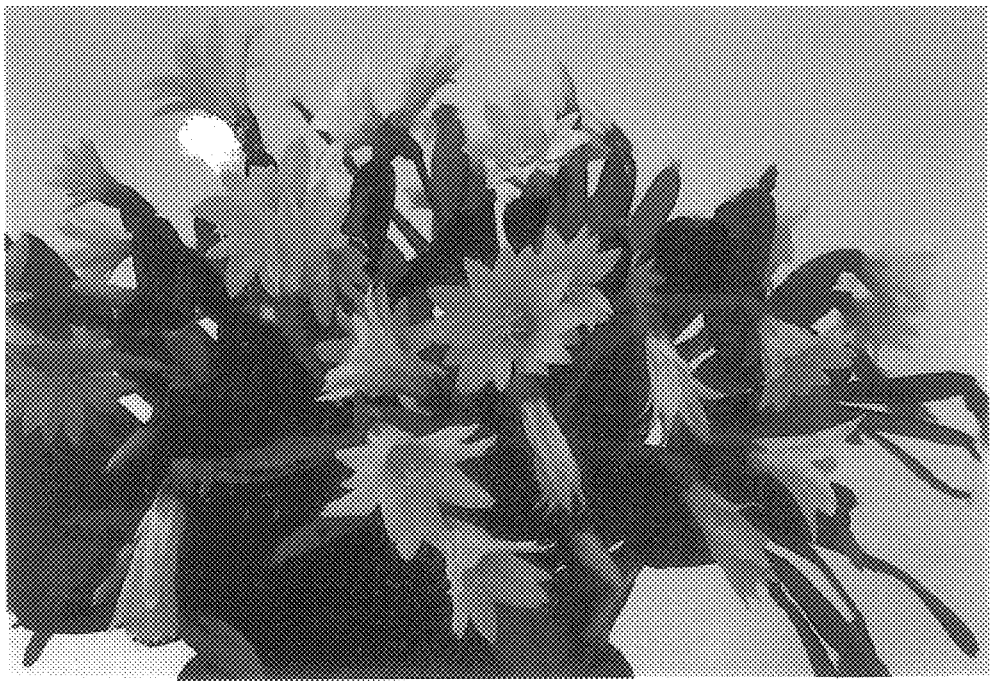
FIG. 3 is a color photograph of several individuals of the new variety illustrating the overall appearance and form of the plants, and the abundance of blooms, when grown in a single pot for commercial sale.
Figure 4:
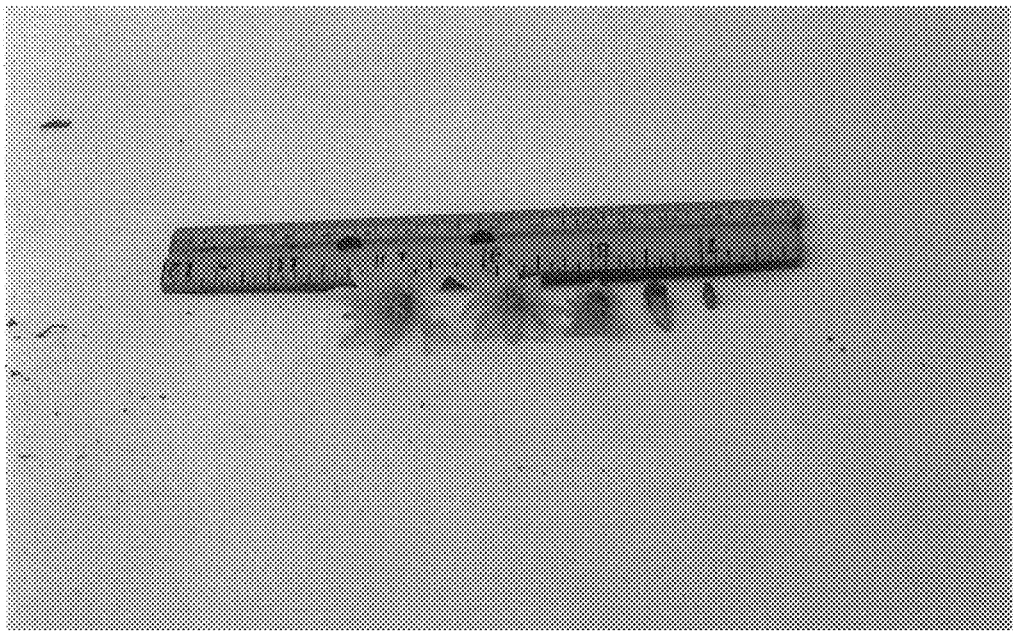
FIG. 4 is a color photograph of several individual flowers of the new variety illustrating the appearance of the bloom in various stages.
Figure 5:
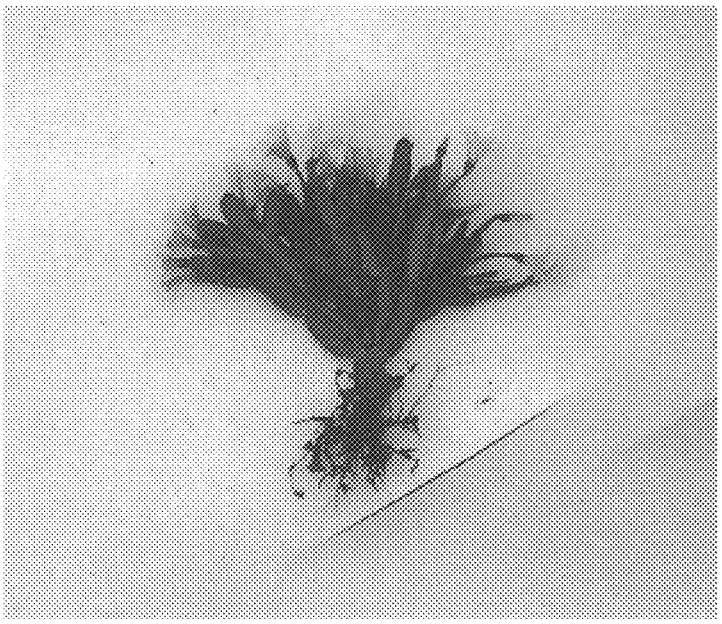
FIG. 5 is a color photograph of one individual plant grown for commercial sale removed from its soil.
Figure 6:
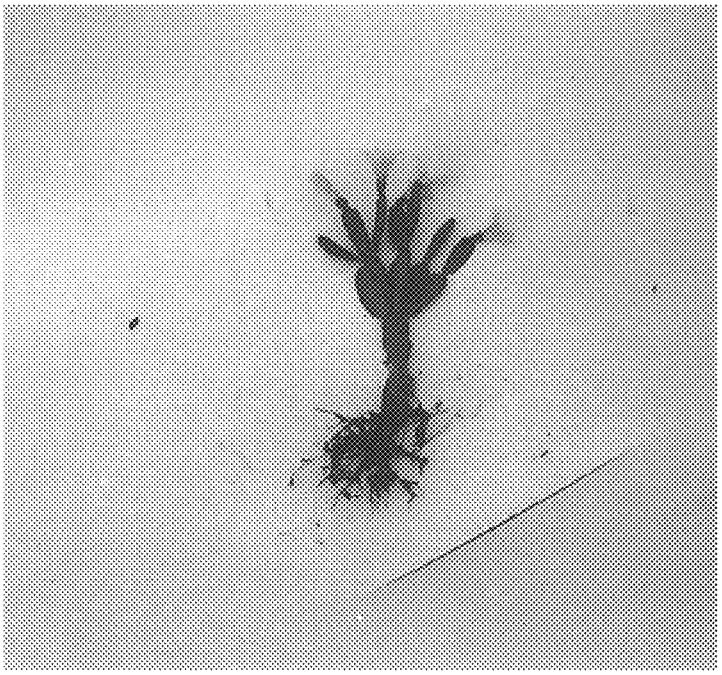
FIG. 6 is a color photograph of an individual plant with all but one of the phylloclades removed from the cutting that was originally planted to show the branching of upper phylloclades on an individual grown for commercial sale.

The following is a detailed description of the new variety. The new variety has not been observed under all possible environmental conditions. Color designation and other values may deviate slightly from the stated values from flowering to flowering, but the deviations will be within the range expected from varying environmental, seasonal and cultural conditions. Color designations were made according to The R.H.S. Color Chart published by The Royal Horticultural Society of London, England.

The plants observed were grown in 4" pots. When the plants were 12 to 18 weeks old, selected, branching phylloclades were removed from the plants by twisting to help the plants grow upright. The plants were approximately 120 mm high. There were typically 4 or 5 cuttings placed in each pot. The following description is based on observations of optimally fertilized plants. The plants were also treated with fungicides and pesticides. The plants were grown under white-washed glass at a commercial nursery in Half Moon Bay, Calif. Temperatures in Half Moon Bay on average range from 55 to 65 degrees Fahrenheit in the summer months, and from 45 to 55 degrees Fahrenheit in the winter months.

As described above the plants, were grown under glass. At night, the plants were kept at an average temperature of approximately 65 degrees Fahrenheit, and during the day, the plants were kept at an average temperature of 74 degrees Fahrenheit. To force the plants to bloom, approximately 15 weeks before the desired blooming period, the plants were cooled by allowing the night-time temperature for the plants to drop below 50 degrees for 8 weeks.

DETAILED PLANT DESCRIPTION

Name: Rhipsalidopsis 'Lauren'.

Parentage: Controlled hybridization of unnamed commercial varieties. One of the early plants used in the hybridization was known to be *Rhipsalidopsis rosea*.

Classification:

*Family.*—Cactaceae.

*Tribe.*—Cereus (Cacteae).

Form: Terrestrial, shade-loving, succulent, leafless plant with jointed and branched stems.

Temperature resistance: Plants can survive temperatures as low as 38 degrees Fahrenheit.

Stems:

*General.*—Irregular stems of multi-branching upright, adventitiously rootable, flattened phylloclades that have a faint midrib. Plants observed had stems that generally consisted of 4 levels of phylloclades, with as many as 8 phylloclades (more commonly 4 or 5) growing from apex of phylloclades at first and second levels, with less at upper levels. Plants observed were 120 mm high.

*Phylloclades.*—General: Mature phylloclades are generally elongated, flattened with no wings, and oblong with entire margins, weakly crenate. Some older basal phylloclades may be sligthly lobed at margins. Immature phylloclades are often not flattened, but four-angled, having multiple ribs terminating at axillary areoles. The apex of the phylloclades are transversely elongated, and areole bearing with compound areoles. The lateral margins typically have three to four spaced axillary areoles. Some phylloclades may have as few as two axillary areoles. Midrib: Faint midrib extends longitudinally of phylloclade and continuously through joints. Texture: Phylloclades have a smooth, waxy epidermis. Wax in basal phylloclades and phylloclades inserted in the ground becoming thick and translucent with age. Size: Phylloclades are usually between 40 mm and 55 mm long, with some as short as 20 mm. Phylloclades bearing flowers can be as short as 32 mm long. Phylloclades are generally 2 mm thick at the midrib, and tapering to 1 mm thick at the margins. Phylloclades are generally 13 mm to 19 mm at their widest point. Color: Mature phylloclades are R.H.S. 137C (yellow-green group) while immature phylloclades are a brighter green: R.H.S. 147C (yellow-green group). Phylloclades have dark margins. Areoles: Terminal areoles — 3 to 5 areoles at apex of phylloclade with many acicular bristles which can be as long as 7 mm and as short as 3 mm. Areoles at apex also have copious, short, brownish to colorless hairs. Typically there is 1 flower at the apex of the uppermost phylloclades. Axiallary areoles — Typically have 3 to 5 acicular bristles without glochidia. Bristles of the axiallary areoles are often shorter than the areoles at the apex of the phylloclades.

Flowers:

*Bloom life.*—The earliest that the plants have been forced to bloom under the growing conditions used is early January. The plants are forced to bloom only once a year. New buds may appear and flower on plants that bloomed in January as late as June. Individual flowers last for 10 to 14 days. Plants appear to be in full bloom for approximately 20 days, when they are forced to bloom in January. Over the 20 day period, individual flowers open in the morning and close slightly at night, closing less and less with each day. As the flowers age, the petals become dessicated but remain attached to gynoecium. Petals and gynoecium eventually fall off phylloclade together.

*General.*—Sessile, actinomorphic, usually solitary, terminal, perfect and epigynous with tepals (undifferentiated whorled sepals and petals) having a spiral emergence as a perianth.

*Perianth.*—General: Free tepals inserted on top of the ovary. Tepals become more reflexed as the flower ages. Shape: Lanceolate with entire margins. Texture: Glabrous. Size: Largest tepals of mature flower are 19 to 25 mm. Fully opened flower generally has a diameter of 31 mm to 38 mm, and consists of 18 tepals. Color: Tepals are thin and semi-transparent. Tepals are darkest at midline of tepal, lightening toward margins. Overall color appearance of tepals is R.H.S. 69A. Darkest portions of tepals are R.H.S 73A, with lighter margins ranging from R.H.S. 62B to white.

*Androecium* (*stamens*).—General: Numerous included stamens with outermost stamens having filaments basally fused to the perianth. Color: Filaments appear darker than the perianth — filaments are R.H.S. 73B, Red-Purple Group, anthers are R.H.S. 9B Yellow Group.

*Gynoecium* (*pistil*).—General: Compound ovary with parietal placentation having a united style, that is exserted past stamens, but inserted in tepals. Style: White at base and R.H.S. 62B Red-Purple Group at top. Style are 16 mm long. Stigma: Exserted and erect with usually 5 or 8 spreading lobes. Color is R.H.S. 158C Yellow-White Group. Ovary: General — Inferior, ovoid, with five angles and generally broadening from insertion to floral end. Generally, mature ovaries are 6 mm long. Fruit: Pome with brown seeds.

I claim:

1. The new and distinct hybrid plant of Cactaceae family substantially as herein shown and described.

* * * * *